(12) United States Patent
Jiang (10) Patent No.: US 10,214,529 B2
(45) Date of Patent: Feb. 26, 2019

(54) SMALL MOLECULES FOR THE TREATMENT OF PRIMARY CANCER AND CANCER METASTASIS

(71) Applicant: Jean X. Jiang, San Antonio, TX (US)

(72) Inventor: Jean X. Jiang, San Antonio, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 15/544,056

(22) PCT Filed: Jan. 15, 2016

(86) PCT No.: PCT/US2016/013645
§ 371 (c)(1),
(2) Date: Jul. 17, 2017

(87) PCT Pub. No.: WO2016/115487
PCT Pub. Date: Jul. 21, 2016

(65) Prior Publication Data
US 2018/0009809 A1   Jan. 11, 2018

Related U.S. Application Data

(60) Provisional application No. 62/104,705, filed on Jan. 17, 2015.

(51) Int. Cl.
| A61K 31/522 | (2006.01) |
| C07D 473/06 | (2006.01) |
| C07D 473/34 | (2006.01) |
| A61P 35/00  | (2006.01) |

(52) U.S. Cl.
CPC .......... *C07D 473/06* (2013.01); *A61K 31/522* (2013.01); *A61P 35/00* (2018.01); *C07D 473/34* (2013.01)

(58) Field of Classification Search
CPC .......................... A61K 31/522; C07D 473/06
USPC ...................................... 514/263.2; 544/268
See application file for complete search history.

(56) References Cited

U.S. PATENT DOCUMENTS

| 2005/0245546 A1 | 11/2005 | Cristalli ..................... 514/263.2 |
| 2006/0116412 A1 | 6/2006 | Ng .............................. 514/394 |
| 2013/0123280 A1 | 5/2013 | Kalla et al. ................ 514/263.2 |
| 2014/0206702 A1 | 7/2014 | Lai ............................... 514/256 |

FOREIGN PATENT DOCUMENTS

| WO | WO 2009/088518 | 7/2009 |
| WO | WO/14/074529 | 5/2014 |

OTHER PUBLICATIONS

Lecka, et al., "Nonhydrolyzable ATP Analogues as Selective Inhibitors of Human NPP1: A Combined Computational/Experimental Study," Journal of Medicinal Chemistry, 56(21), 8308-8320, 2013.

Mao, et al., "Synthesis of Novel Unsymetric Bisbenzimidazoles," Chinese Journal of Chemistry, 28(5), 818-824, 2010.
Nieto, et al., "Synthesis is Novel 1-alkyl-8-substituted-3-(3-Methoxypropyl) Xanthines as Putative A"2"B Receptor Antagonists," Bioorganic & Medicinal Chemistry, 17(9): 3426-3432, 2009.
Partial Supplementary European Search Report Issued in Corresponding PCT Application No. 16737981.7, dated May 28, 2018.
Wei, et al., "3D-Pharmacophore Models for Selective A2A and A2B Adenosine Receptor Antagonists," Journal of Chemical Information and Mode, American Cancer Society, 47(2): 613-625, 2007.
Brown et al. Cancer-associated bone disease. (2007) *Cur. Osteopor. Rep.* 5, 120-127.
Dias et al. The role of Th17/IL-17 on eosinophilic inflammation (2013) *J Autoimmun.* 40:9-20.
International Preliminary Report on Patentability in International Application No. PCT/US2016/013645 dated Jul. 27, 2017.
International Search Report and Written Opinion in International Application No. PCT/US2016/013645 dated Mar. 30, 2016.
Jin et al. Steps in prostate cancer progression that lead to bone metastasis. (2011) *Int. J. Cancer* 128, 2545-2561.
Junquera et al. Clinical experiences with bisphosphonate-associated osteonecrosis of the jaws: analysis of 21 cases. (2009) *Am. J. Otolaryngol.* 30(6), 390-395.
Kohno. Treatment of breast cancer with bone metastasis: bisphosphonate treatment—current and future. (2008) *Int. J. Clin. Oncol.* 13, 18-23.
Ouyang et al. The biological functions of T helper 17 cell effector cytokines in inflammation. (2008) *Immunity.* 28:454-467.
Paget. The Distribution of Secondary Growths in Cancer of the Breast. (1889) *Lancet* 133(3421), 571-573.
Rapaport. Experimental cancer therapy in mice by adenine nucleotides. (1988) *Eur. J. Cancer Clin. Oncol.* 24, 1491-1497.
Rapaport et al. Growth low levels of adenosine inhibition of human tumor cells in soft-agar cultures by treatment with 5'-triphosphate. (1983) *Cancer Res.* 43, 4402-4406.
Roodman. Mechanisms of bone metastasis. (2004) *N. Engl. J. Med.* 350(16), 1655-1664.
Salvestrini et al. Purinergic signaling inhibits human acute myeloblastic leukemia cell proliferation, migration, and engraftment in immunodeficient mice. (2012) *Blood* 119, 217-226.
Shabbir et al. Purinergic receptor-mediated effects of adenosine 5'-triphosphate in urological malignant diseases. (2009) *Int. J. Urol.* 16(2), 143-150.
Truong et al. Bisphosphonate-related osteonecrosis of the jaw presenting as a cutaneous dental sinus tract: A case report and review of the literature. (2010) *J. Am. Acad. Dermatol.* 62, 672-676.
van der Pluijm et al. Monitoring Metastatic Behavior of Human Tumor Cells in Mice with Species-Specific Polymerase Chain Reaction: Elevated Expression of Angiogenesis and Bone Resorption Stimulators by Breast Cancer in Bone Metastases. *J. Bone Miner. Res.* 16, 1077-1091.
Welch et al. Breast cancer metastasis to bone: Evolving models and research challenges. (2003) *J. Musculoskelet. Neuronal Interact.* 3, 30-38.

(Continued)

*Primary Examiner* — Jeffrey H Murray
(74) *Attorney, Agent, or Firm* — Norton Rose Fulbright US LLP (57) ABSTRACT

Certain embodiments and compounds are of the class of non-hydrolysable ATP analogs and adenosine receptor antagonists, useful for inhibiting the migration and growth of cancer cells.

10 Claims, 3 Drawing Sheets

(56) References Cited

OTHER PUBLICATIONS

White et al. P2 receptors and cancer. (2006) *Trends Pharmacol. Sci.* 27(4), 211-217.
Yamagata et al. Targeting Th17 Effector Cytokines for the Treatment of Autoimmune Diseases. (2015) *Arch. Immunol. Ther. Exp. (Warsz.)* 63:405-414.

SMALL MOLECULES FOR THE TREATMENT OF PRIMARY CANCER AND CANCER METASTASIS

This Application is a national phase application under 35 U.S.C. § 371 of International Application No. PCT/US2016/013645, filed Jan. 15, 2016, which claims priority to U.S. Provisional Application Ser. No. 62/104,704 filed Jan. 17, 2015. Both of which are incorporated herein in their entirety.

BACKGROUND

The bone is the most common site of metastasis in patients with advanced cancers including breast and prostate cancers (Jin et al. (2011) *Int. J. Cancer* 128, 2545-2561; Kohno, (2008) *Int. J. Clin. Oncol.* 13, 18-23). Bone metastases are major, potentially fatal complications in patients with advanced cancers. Almost all patients with skeletal metastases have significantly decreased quality of life due to intense pain, pathological fractures, spinal cord compression, and metabolic complications (Welch et al. (2003) *J. Musculoskelet. Neuronal Interact.* 3, 30-38). In fact, post-mortem studies have shown that over 70% of breast cancer patients exhibited skeletal metastases, and only 20% of these patients are still alive five years after the discovery of the metastases (Roodman (2004) *N. Engl. J. Med.* 350, 1655-1664; Welch et al. (2003) *J. Musculoskelet. Neuronal Interact.* 3, 30-38). The high affinity that cancer has for bone is explained by the "seed-and-soil hypothesis", which was proposed over a century ago (Paget (1889) *Lancet* 1, 571-573). It reveals that bone tissues are preferred sites of cancer metastasis due to their microenvironment, which provides a fertile setting in which tumor cells can grow. Many features, such as increased blood flow as well as the release of growth factors from cells in the bone matrix, account for the frequency of bone metastases (van der Pluijm et al. (2001) *J. Bone Miner. Res.* 16, 1077-1091). Thus far, the critical factors and mechanisms responsible for bone metastases are largely unknown.

Bisphosphonate drugs are used to treat bone cancer metastasis and result in decreased tumor growth, reduced bone destruction, and reduced pain (Brown and Guise (2007) *Cur. Osteopor. Rep.* 5, 120-127). Bisphosphonate therapy is associated with adverse side effects, which include atrial fibrillation; arthralgia and osteonecrosis of the jaw; and ophthalmic, dermatologic and renal complications; as well as medication-induced fractures (Junquera et al. (2009) *Am. J. Otolaryngol.* 30, 390-395; Truong et al. (2010) *J. Am. Acad. Dermatol.* 62, 672-676). Despite advances in the diagnosis and treatment of bone metastasis from solid tumors, the mechanism of how bisphosphonate treatment inhibits bone metastasis at the molecular level remains to be established.

Previous studies point to the possibility that ATP through its binding to P2 purinergic receptors exhibits an anti-cancer effect (White and Burnstock (2006) *Trends Pharmacol. Sci.* 27, 211-217). Several studies have established the anti-neoplastic activity of ATP to inhibit the growth of several cell lines, including prostate cancer cells, colon adenocarcinoma cells, melanoma cells, and bladder cancer cells (Rapaport et al. (1983) *Cancer Res.* 43, 4402-4406; Shabbir and Burnstock (2009) *Int. J. Urol.* 16, 143-150; White and Burnstock (2006) *Trends Pharmacol. Sci.* 27, 211-217). The activation of purinergic signaling is also reported to inhibit proliferation and migration of human acute myeloblastic leukemia cells in immune-deficient mice (Salvestrini et al. (2012) *Blood* 119, 217-226). Additionally, in vivo studies show that daily injections of ATP significantly inhibit tumor growth, prolong survival time, and inhibit weight loss in mice (Rapaport (1988) *Eur. J. Cancer Clin. Oncol.* 24, 1491-1497). However, several studies also suggest adverse effects of ATP including increased tumor growth and migration. We recently reported that ATP and ATP analog such as ATPγS inhibits breast cancer cell growth migration and bone metastasis, whereas adenosine and activation of adenosine receptors have opposite effects by promoting growth, migration, and bone metastasis of breast cancer cells (Zhou et al. (2014) *Oncogene* (Epub)).

Non-hydrolysable ATP analog compounds and adenosine receptor antagonist analog compounds can be used for treatment of cancer (WO2014074529). However, there still remains a need for additional non-hydrolysable ATP analog compounds and adenosine receptor antagonists.

SUMMARY

Certain embodiments are directed to non-hydrolysable ATP analogs that inhibit migration and growth of cancer cells. The term non-hydrolysable ATP analog refers to an ATP analog that is not effectively hydrolyzed by ATPase, i.e., the analog is hydrolyzed, if at all, at a rate that is less than 5, 1, or 0.1% of the rate of ATP hydrolysis by ATPase. Certain embodiments are directed to various chemical analogs of the non-hydrolysable ATP analog adenosine 5'-[γ-thio]triphosphate (ATPγS). These chemicals inhibit cancer cell migration and growth. Certain embodiments are directed to chemical analogs of the non-hydrolysable adenosine ATP analog 5'-[γ-thio]triphosphate (ATPγS) having the general formula of Formula: I, including compounds P1-P6 (Table 1)

Formula I where $R_1$ and $R_2$ are selected independently from hydrogen (H), cyano (CN), C1 to C3 alkyl, halogen (fluoro (F), chloro (Cl), bromo (Br), or iodo (I)), or a trifluoromethyl ($CF_3$). In certain aspects R1 is selected from hydrogen, cyano, C1 to C3 alkyl, halogen (fluoro (F), chloro (Cl), bromo (Br), or iodo (I)), or a trifluoromethyl, and R2 is hydrogen or fluoro. In a further aspect R1 is cyano and R2 is H, R1 is H and R2 is H, R1 is trifluoromethyl and R2 is H, R1 is fluoro and R2 is H, R1 is methyl and R2 is H, and R1 is fluoro and R2 is fluoro.

Certain embodiments are directed to administration of one or more compounds of Formula I to treat cancer. The compounds can be administered alone or in combination with other anti-cancer therapies.

Adenosine exposure can promote cancer cell growth and migration, and adenosine is produced by the metabolism of ATP. Certain embodiments are directed to a number of chemical analogs of adenosine receptor antagonist 8-Ethoxy-9-ethyl-9H-purin-6-amine (ANR94, A2A antogonist). These compounds are inhibitors of cancer cell migration and growth. In certain aspects the chemical analogs of adenosine receptor antagonist 8-Ethoxy-9-ethyl-9H-purin-6-amine have a general formula of Formula II, including compounds P7-P10 (Table 1)

Formula II

Certain aspects are directed to compounds of Formula II, where $R_3$ is selected from dihalomethyl, C3 to C5 cycloalkyl, or tetrahydrofuran. In certain aspects R3 is difluoromethyl, cyclopropyl, cyclobutyl, or β-tetrahydrofuran.

Certain embodiments are directed to administration of one or more compounds having a formula of Formula II to treat cancer. The compounds can be administered alone or in combination with compounds with Formula I and/or other anti-cancer therapies.

In certain aspects one or more compounds having a formula of Formula I and/or Formula II are administered to a subject in need of an anti-cancer treatment. In certain aspects the compounds of Formula I and/or Formula II are administered within 1, 5, 10, 20, 30, or 60 minutes or hours of each other. In a further aspect the compounds are administered concurrently. In another aspect one or more compounds of Formula I are administered before, during, or after administration of one or more compounds of Formula II.

TABLE 1

| Compound Code | Structure |
|---|---|
| P1 |  |
| P2 |  |
| P3 |  |
| P4 |  |

List of representative compounds.

TABLE 1-continued

List of representative compounds.

| Compound Code | Structure |
|---|---|
| P5 |  |
| P6 |  |
| P7 |  |
| P8 |  |
| P9 |  |

TABLE 1-continued

List of representative compounds.

| Compound Code | Structure |
| --- | --- |
| P10 |  |

In certain aspects a subject or patient has bladder, blood, bone, bone marrow, brain, breast, colorectal, esophagus, gastrointestinal, head, kidney, liver, lung, nasopharynx, neck, ovary, pancreas, prostate, skin, stomach, testicular, tongue, or uterine cancer. In a further aspect the cancer is a lung, breast, or prostate cancer. In particular aspects the cancer is a metastatic cancer, such as a bone metastasis. In certain aspects the cancer is identified as being at risk for or having a propensity for metastasis or there is no indication that the cancer has yet metastasized. In certain aspects identification of a cancer at risk of metastasis is based on assessment of a tumor biopsy.

In certain embodiments bisphosphonate drugs can be explicitly excluded from the claimed invention due to their potential in vivo toxicity.

As used herein, an "inhibitor" can be a chemical compound that can reduce the activity or function of a protein. An inhibitor, for example, can inhibit directly or indirectly the activity of a protein. Direct inhibition can be accomplished, for example, by binding to a protein and thereby preventing the activity of the protein, or by inhibiting an enzymatic or other activity of the protein competitively, non-competitively, or uncompetitively. Indirect inhibition can be accomplished, for example, by binding to a protein's intended target, such as a receptor or binding partner, thereby blocking or reducing activity of the protein.

The term "effective amount" means an amount effective, at dosages and for periods of time necessary, to achieve the desired therapeutic or prophylactic result. An "effective amount" of an anti-cancer agent in reference to decreasing cancer cell growth or migration, means an amount capable of decreasing, to some extent, the growth of some cancer or tumor cells, or the inhibition of the ability of a cancer or tumor cell to migrate or invade non-tumor tissue, such as bone. The term includes an amount capable of invoking a growth inhibitory, cytostatic, and/or cytotoxic effect, and/or apoptosis of the cancer or tumor cells.

A "therapeutically effective amount" in reference to the treatment of cancer, means an amount capable of invoking one or more of the following effects: (1) inhibition, to some extent, of cancer or tumor growth, including slowing down growth or complete growth arrest; (2) reduction in the number of cancer or tumor cells; (3) reduction in tumor size; (4) inhibition (i.e., reduction, slowing down, or complete stopping) of cancer or tumor cell infiltration into peripheral organs; (5) inhibition (i.e., reduction, slowing down, or complete stopping) of metastasis; (6) enhancement of anti-tumor immune response, which may, but is not required to, result in the regression or rejection of the tumor, or (7) relief, to some extent, of one or more symptoms associated with the cancer or tumor. The therapeutically effective amount may vary according to factors such as the disease state, age, sex and weight of the individual and the ability of one or more anti-cancer agents to elicit a desired response in the individual. A "therapeutically effective amount" is also one in which any toxic or detrimental effects are outweighed by the therapeutically beneficial effects.

The phrases "treating cancer" and "treatment of cancer" mean to decrease, reduce, or inhibit the replication of cancer cells; decrease, reduce or inhibit the spread (formation of metastases) of cancer; decrease tumor size; decrease the number of tumors (i.e. reduce tumor burden); lessen or reduce the number of cancerous cells in the body; prevent recurrence of cancer after surgical removal or other anti-cancer therapies; or ameliorate or alleviate the symptoms of the disease caused by the cancer.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION

Certain embodiments are directed to compounds having a chemical formula of Formula I, for example P1, P2, P3, P4, P4, P5, or P6 (Table 1). These compounds are chemical analogs of non-hydrolysable ATP analog adenosine 5'-[γ-thio]triphosphate (ATPγS).

Other embodiments are directed to compounds having a chemical formula of Formula II, for example P7, P8, P9, or P10, which are chemical analogs of adenosine receptor antagonist 8-Ethoxy-9-ethyl-9H-purin-6-amine (ANR94, A2A antogonist) (Table 1). Studies have shown that all 10 compounds have inhibitory effects on cell migration. In Transwell cell migration assay of MDA-MB-231 human breast cancer cells, all 10 compounds, especially P2, P3, P4, P5 and P9 showed inhibitory effects on cell migration. At 50 µM, none of the compounds exerted any toxicity to the cell.

Figure 1:
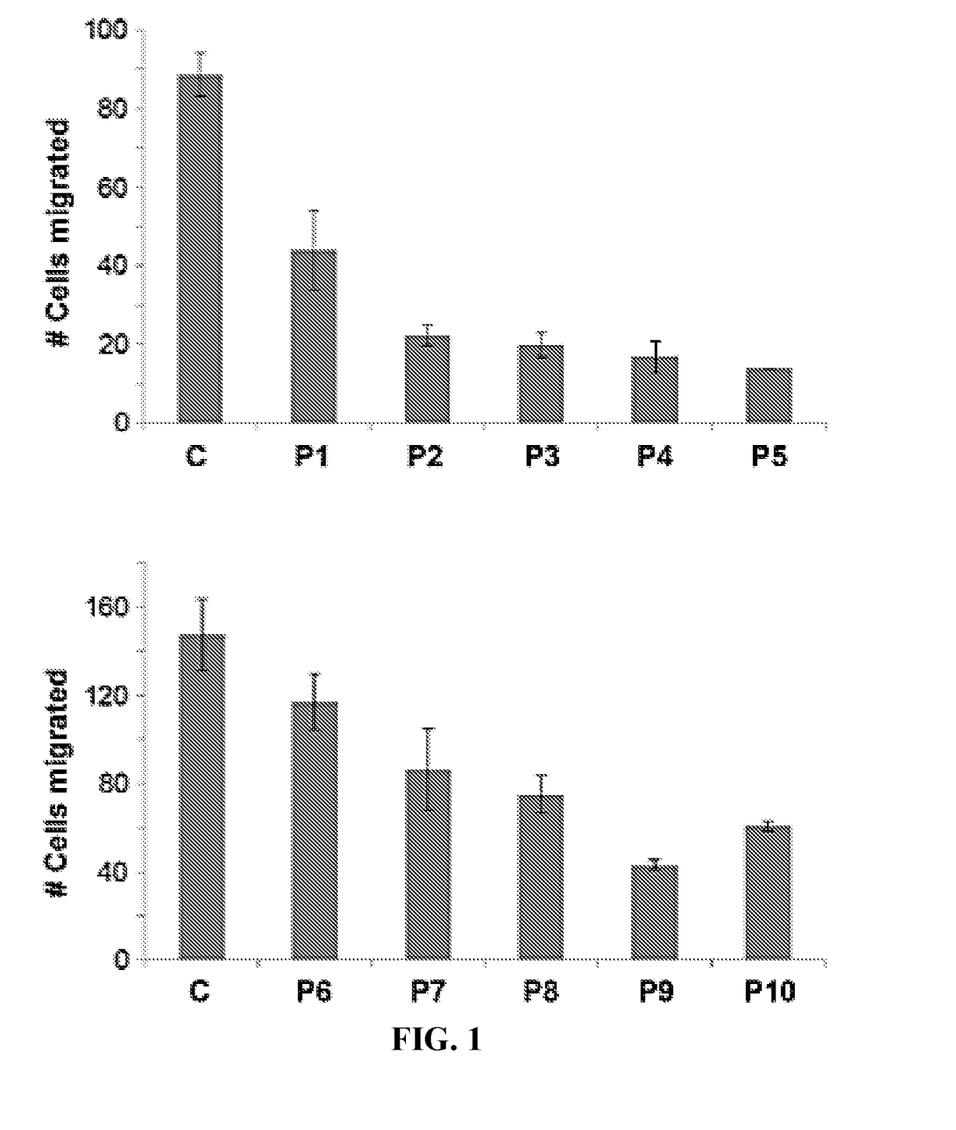
FIG. 1. Transwell cell migration assay with MDA-MB-231 human breast cancer cells.
Figure 2:
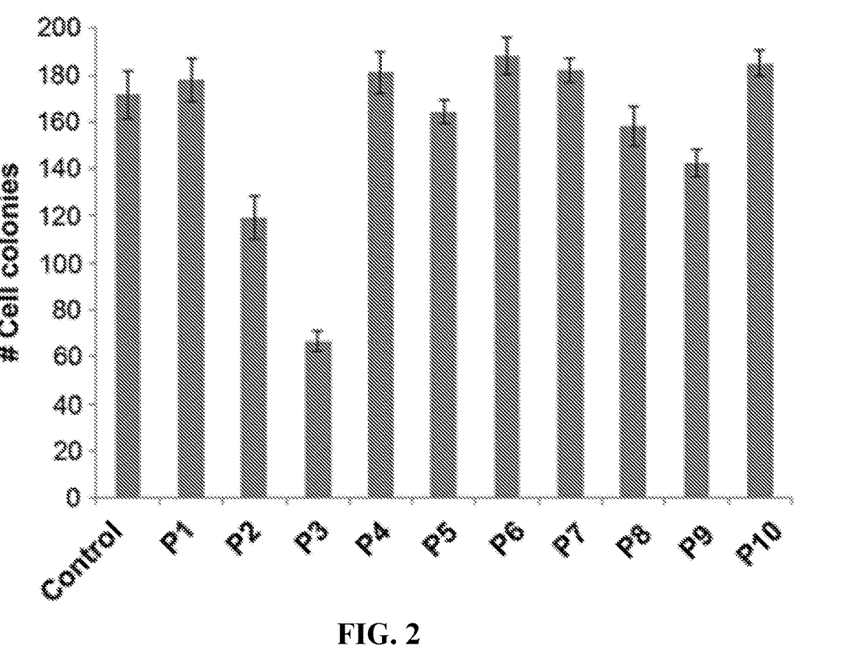
FIG. 2. Soft-agar Anchorage Independent Growth assay of MDA-MB-231 cells

Soft agar assays have been performed to determine anchorage independent cell growth of MDA-MB-231 cells with compounds P1-P10 and compounds P2 and P3 were found to be most effective. There was 30% and 65% decrease in cell colonies as compared to control for P2 and P3 respectively (FIG. 2).

Figure 3:
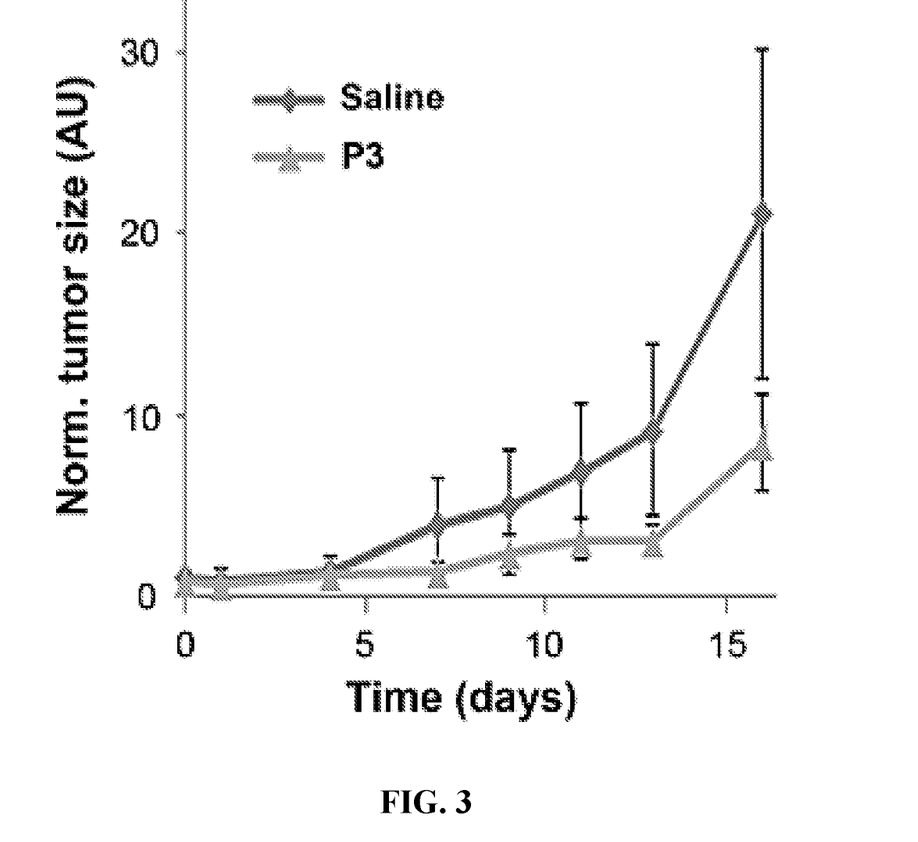
FIG. 3. Mammary Fat Pad Xenograft Assay

In addition, mammary fat pad xenograft assays with MDA-MB-231 cells were performed. MDA-MB-231 cells were xenografted in mammary fat pad of null mice. After tumor nodules appeared, test compounds (e.g., P3) were injected into these mice (500 µl of a 400 µM solution). The tumor size for mice receiving a test compound were compared with control mice (i.e., mice administered vehicle without test compound). After 15 days there was more than 50% reduction in the tumor size for mice received P3 compared to those that did not (FIG. 3).

In certain aspect compounds having Formula I and/or Formula II (e.g., compounds P1-P10) can be used to inhibit proliferation and/or migration of cancer cells. In certain aspects the cancer is a bladder, blood, bone, bone marrow, brain, breast, colorectal, esophagus, gastrointestine, head, kidney, liver, lung, nasopharynx, neck, ovary, pancreas, prostate, skin, stomach, testicular, tongue, or uterine cancer. In a further aspect the cancer is breast cancer. In still a further aspect the cancer is prostate cancer. In particular embodiments the cancer is metastatic cancer, e.g., cancer that has or is at risk of metastasizing or migrating to the bone.

In certain embodiments, the invention also provides compositions comprising one or more compound having the chemical formula of Formula I and/or Formula II (e.g., P1-P2) in a pharmaceutically acceptable formulation. Thus, the use of one or more compound described herein in the preparation of a medicament is also included. Such compositions can be used in the treatment of a variety of cancers. In certain embodiments the treatment is for a metastatic cancer, e.g., lung, breast, or prostate cancer.

The compounds described herein may be formulated into therapeutic compositions in a variety of dosage forms such as, but not limited to, liquid solutions or suspensions, tablets, pills, powders, suppositories, polymeric microcapsules or microvesicles, liposomes, and injectable or infusible solutions. The preferred form depends upon the mode of administration and the particular disease targeted. The compositions also preferably include pharmaceutically acceptable vehicles, carriers, or adjuvants, well known in the art.

Acceptable formulation components for pharmaceutical preparations are nontoxic to recipients at the dosages and concentrations employed. In addition to the compounds described herein, compositions may contain components for modifying, maintaining, or preserving, for example, the pH, osmolarity, viscosity, clarity, color, isotonicity, odor, sterility, stability, rate of dissolution or release, adsorption, or penetration of the composition. Suitable materials for formulating pharmaceutical compositions include, but are not limited to, amino acids (such as glycine, glutamine, asparagine, arginine or lysine); antimicrobials; antioxidants (such as ascorbic acid, sodium sulfite or sodium hydrogen-sulfite); buffers (such as acetate, borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counter ions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (see *Remington's Pharmaceutical Sciences,* 18 th Ed., (A. R. Gennaro, ed.), 1990, Mack Publishing Company), hereby incorporated by reference.

Formulation components are present in concentrations that are acceptable to the site of administration. Buffers are advantageously used to maintain the composition at physiological pH or at a slightly lower pH, typically within a pH range of from about 4.0 to about 8.5, or alternatively, between about 5.0 to 8.0. Pharmaceutical compositions can comprise TRIS buffer of about pH 6.5-8.5, or acetate buffer of about pH 4.0-5.5, which may further include sorbitol or a suitable substitute therefor.

The pharmaceutical composition to be used for in vivo administration is typically sterile. Sterilization may be accomplished by filtration through sterile filtration membranes. If the composition is lyophilized, sterilization may be conducted either prior to or following lyophilization and reconstitution. The composition for parenteral administration may be stored in lyophilized form or in a solution. In certain embodiments, parenteral compositions are placed into a container having a sterile access port, for example, an intravenous solution bag or vial having a stopper pierceable by a hypodermic injection needle, or a sterile pre-filled syringe ready to use for injection.

The above compositions can be administered using conventional modes of delivery including, but not limited to, intravenous, intraperitoneal, oral, intralymphatic, subcutaneous administration, intraarterial, intramuscular, intrapleural, intrathecal, and by perfusion through a regional catheter. Local administration to a tumor or a metastasis in question is also contemplated by the present invention. When administering the compositions by injection, the administration may be by continuous infusion or by single or multiple boluses. For parenteral administration, the agents may be administered in a pyrogen-free, parenterally acceptable aqueous solution comprising the desired compound in a pharmaceutically acceptable vehicle. A particularly suitable vehicle for parenteral injection is sterile distilled water in which one or more anti-cancer agents are formulated as a sterile, isotonic solution, properly preserved.

Once the pharmaceutical composition of the invention has been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

If desired, stabilizers that are conventionally employed in pharmaceutical compositions, such as sucrose, trehalose, or glycine, may be used. Typically, such stabilizers will be added in minor amounts ranging from, for example, about 0.1% to about 0.5% (w/v). Surfactant stabilizers, such as TWEEN®-20 or TWEEN®-80 (ICI Americas, Inc., Bridgewater, N.J., USA), may also be added in conventional amounts.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents. Compositions for parental administration are also sterile, substantially isotonic and made under GMP conditions.

For the compounds described herein, alone or as part of a pharmaceutical composition, such doses are between about 0.001 mg/kg and 1 mg/kg body weight, preferably between about 1 and 100 µg/kg body weight, most preferably between 1 and 10 µg/kg body weight. In certain aspects, compounds described herein can be administered by infusion to patients in daily dosages at rates ranging from 20, 25, 30, 35, 40 to 30, 35, 40, 45, 50 µg/kg/min (including all values and ranges there between) for up to 8 hours, including 1, 2, 3, 4, 5, 6, 7, or 8 hours. Compounds described herein can be administered orally at about 1, 10, 20, 30, 40, 50, 60 to 50, 60, 70, 80 90, 100 µg/kg or mg/kg of body weight per day. In certain aspects the compounds described herein can be administered at about 0.01 to 10 mg/kg of body weight per day.

Therapeutically effective doses will be easily determined by one of skill in the art and will depend on the severity and course of the disease, the patient's health and response to treatment, the patient's age, weight, height, sex, previous medical history and the judgment of the treating physician.

In some methods of the invention, the cancer cell is a tumor cell. The cancer cell may be in a patient. The patient may have a solid tumor. In such cases, embodiments may further involve performing surgery on the patient, such as by resecting all or part of the tumor. Compositions may be administered to the patient before, after, or at the same time as surgery. In additional embodiments, patients may also be administered directly, endoscopically, intratracheally, intratumorally, intravenously, intralesionally, intramuscularly, intraperitoneally, regionally, percutaneously, topically, intrarterially, intravesically, or subcutaneously. Therapeutic compositions may be administered 1, 2, 3, 4, 5, 6, 7, 8, 9, 10, 11, 12, 13, 14, 15, 16, 17, 18, 19, 20 or more times, and they may be administered every 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months.

Methods of treating cancer may further include administering to the patient chemotherapy or radiotherapy, which may be administered more than one time. Chemotherapy includes, but is not limited to, cisplatin (CDDP), carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, taxotere, taxol, transplatinum, 5-fluorouracil, vincristin, vinblastin, methotrexate, gemcitabine, oxaliplatin, irinotecan, topotecan, or any analog or derivative variant thereof. Radiation therapy includes, but is not limited to, X-ray irradiation, UV-irradiation, γ-irradiation, electron-beam radiation, or microwaves. Moreover, a cell or a patient may be administered a microtubule stabilizing agent, including, but not limited to, taxane, as part of methods of the invention. It is specifically contemplated that any of the compounds or derivatives or analogs, can be used with these combination therapies.

Various Chemical Definitions Related to Such Compounds are Provided as Follows.

As used herein, the term the term "fluro" designates —F; the term "cyano" means —CN; the term "methyl" means —CH$_3$; the term "difluromethyl" means —CF$_2$H; the term "trifluromethyl" means —CF$_3$; the term "cyclopropyl" means a three membered saturated cycloalkyl ring; the term "cyclobutyl" means four membered saturated cycloalkyl ring; and the term "β-tetrahydrofuran" means a five membered saturated heterocyclyl ring with O as heteroatom and is substituted at the β carbon from the heteroatom.

As used herein, the term "halo" designates —F, —Cl, —Br or —I; the term "mercapto" means —SH; the term "cyano" means —CN; the term "azido" means —N$_3$; and the term "hydroxy" means —OH.

The term "alkyl," by itself or as part of another substituent, means, unless otherwise stated, a linear (i.e. unbranched) or branched carbon chain, which may be fully saturated, mono- or polyunsaturated. An unsaturated alkyl group is one having one or more double bonds or triple bonds. Saturated alkyl groups include those having one or more carbon-carbon double bonds (alkenyl) and those having one or more carbon-carbon triple bonds (alkynyl). The groups, —CH$_3$ (Me), —CH$_2$CH$_3$ (Et), —CH$_2$CH$_2$CH$_3$ (n-Pr), —CH(CH$_3$)$_2$ (iso-Pr), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neo-pentyl), are all non-limiting examples of alkyl groups.

The term "heteroalkyl," by itself or in combination with another term, means, unless otherwise stated, a linear or branched chain having at least one carbon atom and at least one heteroatom selected from the group consisting of O, N, S, P, and Si. In certain embodiments, the heteroatoms are selected from the group consisting of O and N. The heteroatom(s) may be placed at any interior position of the heteroalkyl group or at the position at which the alkyl group is attached to the remainder of the molecule. Up to two heteroatoms may be consecutive. The following groups are all non-limiting examples of heteroalkyl groups: trifluoromethyl, —CH$_2$F, —CH$_2$Cl, —CH$_2$Br, —CH$_2$OH, —CH$_2$OCH$_3$, —CH$_2$OCH$_2$CF$_3$, —CH$_2$OC(O)CH$_3$, —CH$_2$NH$_2$, —CH$_2$NHCH$_3$, —CH$_2$N(CH$_3$)$_2$, —CH$_2$CH$_2$Cl, —CH$_2$CH$_2$OH, CH$_2$CH$_2$OC(O)CH$_3$, —CH$_2$CH$_2$NHCO$_2$C(CH$_3$)$_3$, and —CH$_2$Si(CH$_3$)$_3$.

The terms "cycloalkyl" and "heterocyclyl," by themselves or in combination with other terms, means cyclic versions of "alkyl" and "heteroalkyl", respectively. Additionally, for heterocyclyl, a heteroatom can occupy the position at which the heterocycle is attached to the remainder of the molecule.

The term "aryl" means a polyunsaturated, aromatic, hydrocarbon substituent. Aryl groups can be monocyclic or polycyclic (e.g., 2 to 3 rings that are fused together or linked covalently). The term "heteroaryl" refers to an aryl group that contains one to four heteroatoms selected from N, O, and S. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

Various groups are described herein as substituted or unsubstituted (i.e., optionally substituted). Optionally substituted groups may include one or more substituents independently selected from: halogen, nitro, cyano, hydroxy, amino, mercapto, formyl, carboxy, oxo, carbamoyl, substituted or unsubstituted alkyl, substituted or unsubstituted heteroalkyl, alkoxy, alkylthio, alkylamino, (alkyl)$_2$amino, alkylsulfinyl, alkyl sulfonyl, arylsulfonyl, substituted or unsubstituted cycloalkyl, substituted or unsubstituted heterocyclyl, substituted or unsubstituted aryl, and substituted or unsubstituted heteroaryl. In certain aspects the optional substituents may be further substituted with one or more substituents independently selected from: halogen, nitro, cyano, hydroxy, amino, mercapto, formyl, carboxy, carbamoyl, unsubstituted alkyl, unsubstituted heteroalkyl, alkoxy, alkylthio, alkylamino, (alkyl)$_2$amino, alkylsulfinyl, alkyl sulfonyl, aryl sulfonyl, unsubstituted cycloalkyl, unsubstituted heterocyclyl, unsubstituted aryl, or unsubstituted heteroaryl. Exemplary optional substituents include, but are not limited to: —OH, oxo (=O), —Cl, —F, Br, C$_{1-4}$alkyl, phenyl, benzyl, —NH$_2$, —NH(C$_{1-4}$alkyl), —N(C$_{1-4}$alkyl)$_2$, —NO$_2$, —S(C$_{1-4}$alkyl), —SO$_2$(C$_{1-4}$alkyl), —CO$_2$(C$_{1-4}$alkyl), and —O(C$_{1-4}$alkyl).

The term "pharmaceutically acceptable salts," as used herein, refers to salts of compounds of this invention that are substantially non-toxic to living organisms. Typical pharmaceutically acceptable salts include those salts prepared by reaction of a compound of this invention with an inorganic or organic acid, or an organic base, depending on the substituents present on the compounds of the invention.

Non-limiting examples of inorganic acids which may be used to prepare pharmaceutically acceptable salts include: hydrochloric acid, phosphoric acid, sulfuric acid, hydrobromic acid, hydroiodic acid, phosphorous acid and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydro fluoride, acetate, propionate, formate, oxalate, citrate, lactate, p-toluenesulfonate, methanesulfonate, maleate, and the like.

Suitable pharmaceutically acceptable salts may also be formed by reacting the agents of the invention with an organic base such as methylamine, ethylamine, ethanolamine, lysine, ornithine and the like. Pharmaceutically acceptable salts include the salts formed between carboxylate or sulfonate groups found on some of the compounds of this invention and inorganic cations, such as sodium, potassium, ammonium, or calcium, or such organic cations as isopropylammonium, trimethylammonium, tetramethylammonium, and imidazolium.

It should be recognized that the particular anion or cation forming a part of any salt of this invention is not critical, so long as the salt, as a whole, is pharmacologically acceptable.

Additional examples of pharmaceutically acceptable salts and their methods of preparation and use are presented in Handbook of Pharmaceutical Salts: Properties, Selection and Use (2002), which is incorporated herein by reference.

It is contemplated that any embodiment discussed in this specification can be implemented with respect to any method or composition of the invention, and vice versa. Furthermore, compositions of the invention can be used to achieve methods of the invention.

EXAMPLES

The following examples as well as the figures are included to demonstrate preferred embodiments of the invention. It should be appreciated by those of skill in the art that the techniques disclosed in the examples or figures represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

A. Materials & Methods

Cell Lines and Cell Cultures.

MDA-MB-231 cells were grown in McCoy's 5A Modified Media (Gibco) supplemented with 10% FBS (Hyclone). Py8119 cells were grown in F12K nutrient media (Gibco) supplemented with 5% Fetal Clone II (Fisher Scientific). All cell lines were incubated in a 5% $CO_2$ incubator at 37° C.

Cell Migration Assay.

Migration assays were performed in transwell membrane filter inserts in 24-well tissue culture plates (BD Biosciences San Jose, Calif., USA). The transwell membrane filter inserts contained 6.5-mm diameter, 8-μm pore size, 10-nm thick polycarbonate membranes. Five-hundred microliter breast cancer cell suspensions were added to the upper side of the inserts at a density of $10 \times 10^4$ cells/insert and 750 μl CM with or without other compounds was added to the lower wells. Cells were incubated at 37° C. for 18-20 hr. Cells that did not migrate through the filters were removed using cotton swabs, and cells that migrated through the inserts were fixed and stained with Hema 3 Stat Pack (Fisher Scientific). The number of migrated cells in 5 fields of view per insert was counted under a light microscope at magnification 10×.

Soft Agar Colony Formation Assay.

For anchorage-independent cell growth, MDA-MB-231 cells were plated in 0.4% agarose with complete medium supplemented with 50 μM compound (P1 to P10) on top of a 0.8% agarose base supplemented with complete medium. Cells were maintained for about 2 weeks before staining with p-iodonitrotetrazolium violet (Sigma-Aldrich, St. Louis, Mo.). Images were captured by using a scanner and the numbers of colonies were counted.

Animals.

Four-week-old female athymic nude mice (Harlan Sprague-Dawley, Indianapolis, Ind., USA) were used for the mammary fat pad injections. Four- to five-week old female C57bl/6 mice were used for the intratibial injections. Animals were maintained under the care and supervision of the Laboratory Animal Research facility at the University of Texas Health Science Center, San Antonio, Tex. The animal protocol was approved and monitored by the Institutional Animal Care and Use Committee.

In Vivo Xenograft Experiment.

MDA-MB-231 cells were injected subcutaneously in the mammary fat pad of 4-week-old female nu/nu athymic nude mice. Each mouse received bilateral subcutaneous inoculation in both the left and right inguinal mammary fat pad areas with 100 μl of cell suspension containing ~$1 \times 10^7$ cells/ml in serum-free media. Animals were randomly assigned to 3 different groups, and solid tumors were allowed to form up to about 5 $mm^3$ volume before treatments began. Compound P3 400 μmol/500 μl saline, or saline as a control was administered intraperitoneally (IP) three times a week for 3 weeks. The growth of xenograft tumors was monitored twice a week and tumor size was measured with a caliper in two dimensions. Tumor volumes were calculated with the equation $V=(L \times W^2) \times 0.5$ ($mm^3$), where L is length and W is width of a tumor.

Statistical Analysis.

Unless otherwise specified in the Figure Legends, the data are presented as the mean±S.E.M. of at least three determinations. Asterisks indicate the degree of significant differences compared with the controls (*, $P<0.05$; , $P<0.01$; *, $P<0.001$). One-way analysis of variance (ANOVA) and Student Newman-Keuls test were used to compare groups using GraphPad Prism 5.04 software (GraphPad).

The invention claimed is:

1. A compound that is a chemical analog of non-hydrolysable adenosine ATP analog 5'-[γ-thio]triphosphate (ATPγS) with general formula of Formula I:

Formula I where $R_1$ and $R_2$ are independently selected from hydrogen, cyano, C1 to C3 alkyl, halo, or heteromethyl.

2. The compound of claim 1, wherein $R_1$ is selected from hydrogen, cyano, C1 to C3 alkyl, halo, or heteromethyl, and $R_2$ is a hydrogen or halogen.

3. The compound of claim 2, wherein $R_1$ is a hydrogen, fluoro, methyl, cyano, or trifluoromethyl.

4. The compound of claim 1, wherein $R_1$ is cyano and $R_2$ is hydrogen, $R_1$ is hydrogen and $R_2$ is hydrogen, $R_1$ is trifluoromethyl and $R_2$ is hydrogen, $R_1$ methyl and $R_2$ is hydrogen, and or $R_1$ is fluoro and $R_2$ is fluoro.

5. A method for inhibiting migration of breast cancer cells in a breast cancer patient comprising administering to the patient an effective amount of a one or more compounds of claim 1.

6. The method of claim 5, wherein one or more compounds of claim 1 are administered intravenously.

7. The method of claim 5, wherein one or more compounds of claim 1 are administered orally.

8. A compound that is a chemical analog of adenosine receptor antagonist 8-Ethoxy-9-ethyl-9H-purin-6-amine with general formula of Formula II Formula II where $R_3$ is a heteromethyl, cycloalkyl, or tetrahydrofuran.

9. The compound of claim 8, wherein $R_3$ is difluoro methyl, cyclopropyl, cyclobutyl, or β-tetrahydrofuran.

10. A method for inhibiting migration of breast cancer cells in a breast cancer patient comprising administering to the patient an effective amount of a one or more compounds of claim 8.

* * * * *